United States Patent
Alexandre et al.

(10) Patent No.: US 7,500,960 B2
(45) Date of Patent: Mar. 10, 2009

(54) NEEDLELESS INJECTION DEVICE COMPRISING A PYROTECHNIC CARTRIDGE, AND METHOD OF ASSEMBLING SUCH A DEVICE

(75) Inventors: Patrick Alexandre, Gray (FR); Georges Baud, La Crau (FR); Bernard Brouquieres, Toulon (FR); Philippe Gautier, Le Plessis Pate (FR)

(73) Assignee: Crossject, Paris (FR)

( * ) Notice: Subject to any disclaimer, the term of this patent is extended or adjusted under 35 U.S.C. 154(b) by 91 days.

(21) Appl. No.: 10/551,652

(22) PCT Filed: Mar. 18, 2004

(86) PCT No.: PCT/FR2004/000658

§ 371 (c)(1),
(2), (4) Date: Sep. 29, 2005

(87) PCT Pub. No.: WO2004/084975

PCT Pub. Date: Oct. 7, 2004

(65) Prior Publication Data

US 2006/0247573 A1 Nov. 2, 2006

(30) Foreign Application Priority Data

Mar. 21, 2003 (FR) .................................. 03 03497

(51) Int. Cl.
*A61M 5/30* (2006.01)
(52) U.S. Cl. ....................................................... 604/69
(58) Field of Classification Search ................... 604/68, 604/69, 71, 72, 232
See application file for complete search history.

(56) References Cited

U.S. PATENT DOCUMENTS

| | | | |
|---|---|---|---|
| 3,688,765 A | 9/1972 | Gasaway | |
| 3,802,430 A * | 4/1974 | Schwebel et al. | 604/69 |
| 4,652,261 A | 3/1987 | Mech et al. | |
| 4,790,824 A | 12/1988 | Morrow et al. | |
| 4,941,880 A | 7/1990 | Burns | |
| 5,520,639 A | 5/1996 | Peterson et al. | |
| 5,730,723 A * | 3/1998 | Castellano et al. | 604/68 |
| 5,865,795 A | 2/1999 | Schiff et al. | |
| 6,328,714 B1 * | 12/2001 | Bellhouse et al. | 604/232 |
| 2002/0188250 A1 * | 12/2002 | Landau et al. | 604/70 |
| 2004/0162517 A1 * | 8/2004 | Furst et al. | 604/69 |

FOREIGN PATENT DOCUMENTS

| | | |
|---|---|---|
| FR | 2 815 544 A1 | 4/2002 |
| WO | WO 97/47730 A1 | 12/1997 |
| WO | WO 00/48654 A1 | 8/2000 |

\* cited by examiner

*Primary Examiner*—Kevin C Sirmons
*Assistant Examiner*—Elizabeth R Macneill
(74) *Attorney, Agent, or Firm*—Oliff & Berridge, PLC

(57) ABSTRACT

The invention relates to a method of assembling a needleless injection device (1), whereby a plurality of elements forming a circuit of elements is assembled to a body (2). The aforementioned circuit comprises elements such as an initiation device, a receptacle (5) containing an active agent to be injected, and an active agent injection system. The inventive method is characterised in that it comprises a step in which a gas-generating cartridge (6), which is adapted to the nature and/or quantity of active agent to be injected as well as to the skin penetration depth desired for same, is inserted directly into the circuit of elements, independently of said elements, from outside the body (2). The invention also relates to a needleless injection device (1).

12 Claims, 2 Drawing Sheets

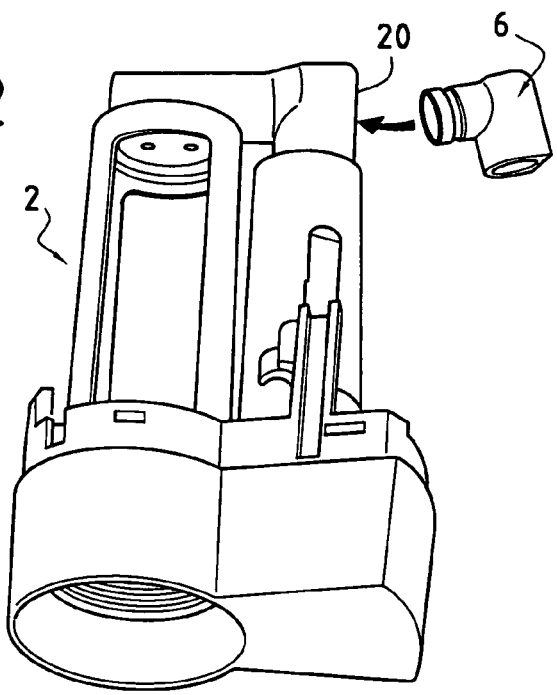
FIG.2
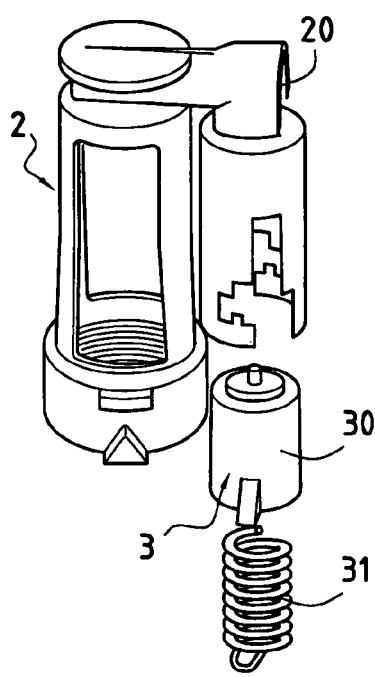
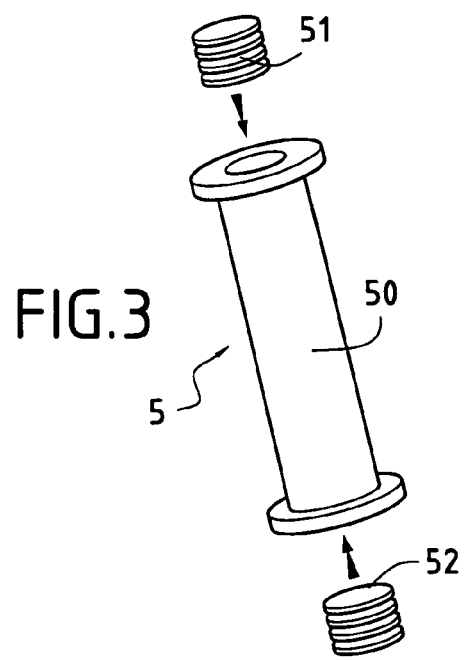
FIG.3
FIG.1
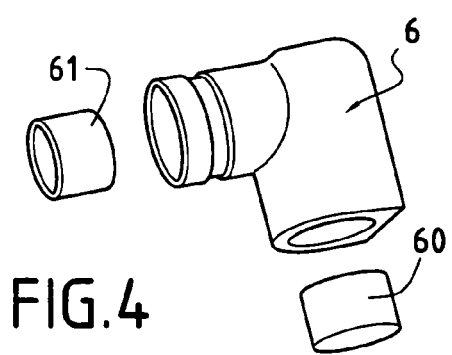
FIG.4
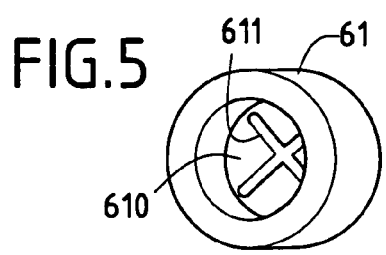
FIG.5

NEEDLELESS INJECTION DEVICE COMPRISING A PYROTECHNIC CARTRIDGE, AND METHOD OF ASSEMBLING SUCH A DEVICE

BACKGROUND

The technical field of the invention is that of prefilled and disposable needleless injection devices functioning with a gas generator and used for intradermal, subcutaneous and intramuscular injections of liquid active principle for therapeutic use in human or veterinary medicine.

The active principle is composed of a more or less viscous liquid, a mixture of liquids, or a gel. The active principle can also be a solid dissolved in a suitable solvent for injection or can be a powdered solid in suspension at a certain concentration in a suitable liquid. The particle size of the active principle must then be compatible with the diameter of the conduits so as to avoid blocking them.

In the prior art, needleless injection devices have already been the subject of several patent applications.

Patent application WO 00/46854 relates to a disposable needleless injection device for injecting a variable quantity of liquid active principle. This device more particularly comprises a reservoir of liquid in which a piston is placed for pushing the liquid through an injection system. This device includes a reserve of gas and a device allowing this reserve of gas to be pierced so as to release the gases necessary for pushing the piston present in the reservoir of liquid and thus eject the liquid out of the device. Depending on the nature and/or quantity of liquid active principle to be injected for the particular treatment and depending on the depth of skin penetration desired for said active principle, it is necessary to be able to adapt the quantity of gas to be generated. In the case of a prefilled and needleless injection device ready for use by the user, this choice will have to be made definitively during the process of assembling the device.

In the process of assembling a device of the kind disclosed in patent application WO 00/48654, the gas reserve is positioned, in a first stage, in the body of the device, after which, in a subsequent stage, the reservoir of liquid to be injected is fixed on said body. The compulsory sequence of these two stages is particularly restrictive insofar as it is impossible to easily adapt the quantity of gas present in the gas reserve to the nature and/or quantity of liquid to be injected and to the desired depth of penetration.

The U.S. Pat. No. 4,941,880 discloses a needleless injection device in which a reserve of gas is screwed onto one end of the device independently of the reservoir of liquid. However, the reserve of gas can be fitted onto the device only when the system for piercing the reserve of gas is arranged in the body. This constraint will therefore have to be taken into consideration when assembling such a device.

Moreover, in a device of this kind, it may prove dangerous to fix the reserve of gas onto one end of this device, since said reserve of gas is then easily accessible to the user and may well be damaged.

SUMMARY

It is an object of the invention to ensure that, during the process of assembling a needleless injection device, there are no constraints with regard to fitting the gas-generating part onto the device. Another object of the invention is to ensure that fitting the gas-generating part onto the device is not done in a way that makes the gas-generating part easily accessible to the user once the device has been fully assembled.

This objective is achieved by a method of assembling a needleless injection device, comprising steps in which a plurality of elements forming a circuit of elements are assembled on a body, this circuit in particular comprising an initiation device, a reservoir containing an active principle to be injected, and a system for injecting the active principle, this method being characterized in that it comprises a step in which a gas-generating cartridge adapted to the nature and/or quantity of the active principle to be injected and to the depth of skin penetration desired for said active principle is inserted from the outside of the body and directly into the circuit of elements, independently of said elements.

According to the invention, it will therefore be possible, by acting on the nature and/or quantity of gas to be generated, to produce, on one and the same assembly line, needleless injection devices in which the nature and/or quantity of the liquid active principle to be injected differ. The quantity of gas to be generated must also be adapted as a function of the depth of penetration to be obtained for the active principle that is to be injected.

The object of the invention as defined above is also achieved by a needleless injection device comprising a body supporting or delimiting a plurality of elements forming a circuit of elements, this circuit comprising an initiation device, a gas-generating cartridge, a reservoir containing an active principle to be injected, and a system for injecting the active principle, this device being characterized in that the body comprises a seat intended to receive said cartridge, said seat being accessible from the outside so that it is possible to insert the cartridge directly into the circuit of elements, independently of the other elements.

According to the invention, therefore, there is no constraint on the nature and/or quantity of the liquid active principle intended to be placed in the device, nor on the depth of skin penetration desired for said active principle. Thus, it will be possible to individualize the needleless injection device as late as the process of assembling it, that is to say it will be possible to easily adapt the quantity of gas to be generated as a function of the nature and/or quantity of active principle to be injected and as a function of the desired depth of penetration of said active principle. Moreover, the gas-generating cartridge is inserted into the circuit of elements in a seat of the body and is therefore not easily accessible to the user.

According to a preferred embodiment, the body includes an opening communicating with the seat. According to the invention, the body thus includes a specific independent opening communicating with the seat in which the gas-generating cartridge is inserted. Thus, the gas-generating cartridge will be able to be positioned in the circuit of elements at any stage in the process of assembling the body of the device, and thus independently of the assembling of the other elements on the body.

According to a particular feature, the cartridge, once in place in the seat, closes off the opening so as to seal it from the outside.

According to another particular feature, the seat is placed between the initiation device and the reservoir containing the liquid active principle.

According to a preferred embodiment, the cartridge has the form of a conduit which, once in place in the seat, contributes to forming a connection between the elements situated upstream and the elements situated downstream.

According to another particular feature, the circuit of elements follows an inverted U-shape including two parallel branches interconnected by a perpendicular transverse branch.

According to another particular feature, the introduction of the cartridge into the circuit is done perpendicular to the axis of symmetry of the U formed by the circuit.

According to another particular feature, the cartridge has an L-shape, and, once it has been inserted, its shape follows a right angle present between one of the parallel branches of the inverted U, formed by the circuit, and its transverse branch.

According to a preferred embodiment, the gas-generating cartridge is a pyrotechnic cartridge comprising a pyrotechnic charge. According to the invention, the insertion of the pyrotechnic charge into the device will be able to be done at any stage of the process of assembling the body of the device and in particular toward the end of this process, which will make it possible both to adapt the pyrotechnic charge to the desired depth of penetration and to the nature and/or quantity of active principle present in the device, and also to limit the manipulations of the pyrotechnic charge during the process of assembling the device and thus to reduce the risks of untimely initiation of the charges throughout the assembly process.

According to a particular feature of this latter preferred embodiment, the cartridge comprises a primer.

According to another particular feature, the cartridge has the shape of an L-shaped conduit in which the pyrotechnic charge is placed, this conduit being closed off at one of its ends by the primer and at its other end by a burstable sealing disk.

According to another particular feature, the device for initiating the pyrotechnic charge includes a percussion device for striking the primer. The percussion device will, for example, be formed by a striker actuated with the aid of a spring.

According to another particular feature, the seat of the body, able to receive the cartridge, is placed between the percussion device and a gas expansion chamber situated upstream of the reservoir.

According to another particular feature, the body comprises a first hollow part and a second hollow part which are arranged on two parallel axes and are connected by a conduit, this conduit delimiting the seat of the cartridge and the gas expansion chamber.

According to another particular feature, the cartridge is placed in the seat of the body in such a way that the primer is situated on the axis of the percussion device and the sealing disk is situated on the axis of the gas expansion chamber.

BRIEF DESCRIPTION OF THE DRAWINGS

The invention, with its characteristics and advantages, will become clearer from reading the description given with reference to the attached drawings, in which:

FIG. 1 depicts, in perspective and in an exploded view, the body of the device together with certain elements intended to be assembled on the body of the device.

FIG. 2 depicts, in perspective, the body of the device onto which certain elements have been assembled, together with the gas-generating cartridge.

FIG. 3 depicts, in perspective and in an exploded view, the reservoir intended to receive the liquid active principle.

FIG. 4 depicts, in perspective and in an exploded view, a pyrotechnic gas-generating cartridge used in the device according to the invention.

FIG. 5 depicts, in perspective, a burstable sealing disk as used in the pyrotechnic cartridge of FIG. 4.

DESCRIPTION

Figure 6:
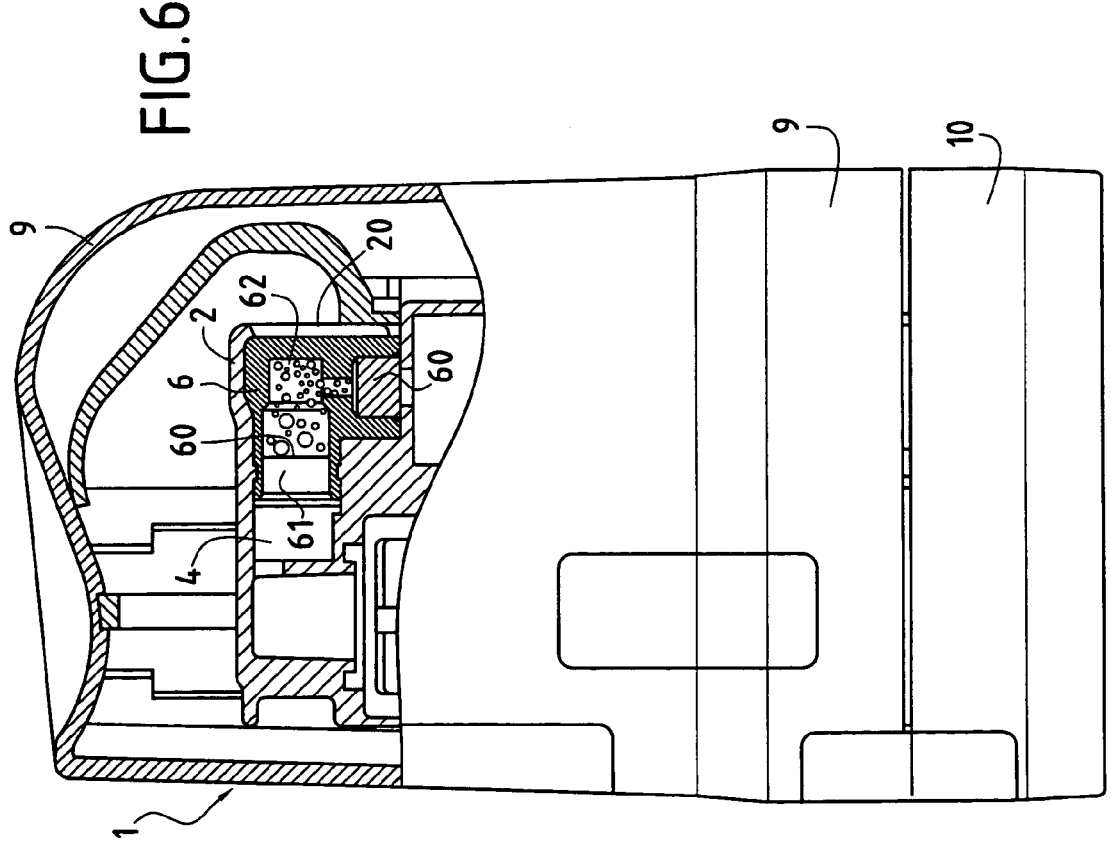
FIG. 6 depicts, in a partial longitudinal section, a needleless injection device according to the invention in the nonactivated position, in which the pyrotechnic cartridge shown in FIG. 4 is inserted.

A needleless injection device 1 according to the invention, depicted in FIG. 6, comprises a hollow body 2 in the shape of an inverted U inserted under a cap 9 for actuating the device 1, this cap being closed off by a stopper 10. This U-shape gives the device a compact form, the advantages of which are more particularly described in patent No. FR 2 815 544. Actuation of such a device 1 by the patient, using the cap 9, is also described in patent FR 2 815 544. During the process of assembling the device 1, this body 2 is intended to receive a plurality of elements. Thus, once assembled, the body 2, depicted in FIG. 1, comprises or delimits successively, from upstream to downstream, a percussion device 3 comprising a striker 30 and a spring 31, a primer 60, and a pyrotechnic charge 62, these three elements forming a gas generator, a gas expansion chamber 4, a reservoir 5 (FIG. 3) containing a liquid active principle to be injected, and an injection system (not visible). The gas generator constitutes a first linear subassembly inserted into the body 2 along a first vertical branch of the inverted U formed by the body 2. The reservoir 5, containing the active principle to be injected, and the injection system form a second linear subassembly inserted along the second vertical branch of the inverted U formed by the body 2. The first and second subassemblies are linear along two parallel axes (A1, A2, FIG. 7) and are connected to one another by the gas expansion chamber 4 which is formed in the body 2 along an axis perpendicular to the axes (A1, A2) of the two subassemblies, that is to say along the transverse branch connecting the two parallel branches of the inverted U formed by the body 2.

The reservoir 5 depicted in FIG. 3 is, for example, formed by a glass tube 50 open at both ends. The tube 50 is inserted into the body 2 in such a way as to be connected, at its most upstream end, to the gas expansion chamber 4, and, at its most downstream end, to the injection system. The active principle (not shown) is, for example, held captive in the glass tube 50 between an upstream piston plug 51 and a downstream piston plug 52 which are inserted into the tube 50. The upstream 51 and downstream 52 piston plugs are made, for example, of an elastomer-based deformable material. The injection system comprises in particular an injection nozzle through which the active principle contained in the reservoir 5 is injected. This injection nozzle comprises, for example, a plurality of injection channels along which the liquid is intended to pass at the time of injection.

Figure 7:
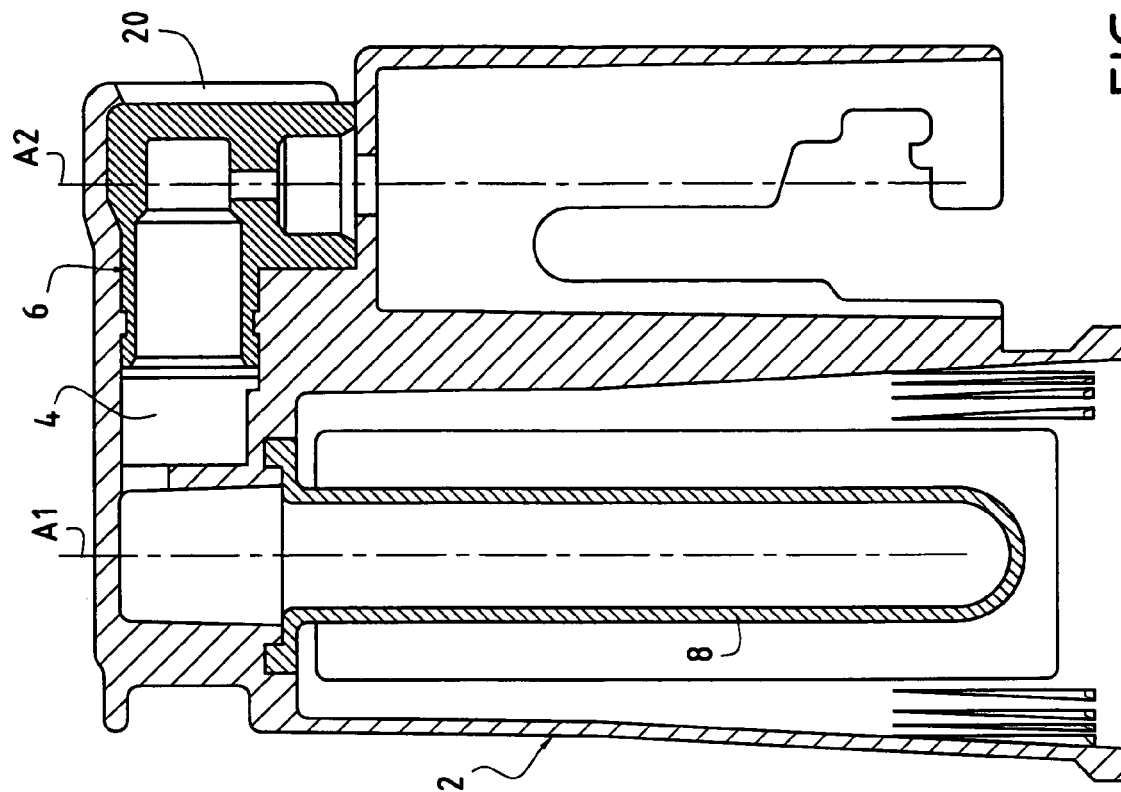
FIG. 7 depicts, in longitudinal section, the body of the device which has functioned and in which an empty pyrotechnic cartridge 4 can be seen.

According to the invention, the gas generator comprises a gas-generating cartridge 6 and a percussion device 3. The gas-generating cartridge 6 depicted in FIGS. 2 and 4 is made of metal, for example, and comprises a primer 60 and a pyrotechnic charge 62 (FIG. 6) making it possible to generate the quantity of gas required to bring about the injection of the active principle. The primer 60 is, for example, of the kind used in a cartridge for a hunting gun. The pyrotechnic charge 62 is composed of a powder able to emit a large quantity of gas, for example a simple nitrocellulose-based powder. With reference to FIG. 4, the gas-generating cartridge 6 used in the needleless injection device 1 according to the invention is, for example, in the form of an L-shaped conduit in which the pyrotechnic charge 62 is placed. When the cartridge 6 is fitted into the device 1, as depicted in FIG. 6, the most upstream end of the conduit forming the cartridge is closed off by the primer 60 while the most downstream end of this conduit is closed off by a burstable sealing disk 61 shown in more detail in FIG. 5. This sealing disk 61 is in the form of a cylindrical plug engaged in the channel of the conduit formed by the cartridge 6. This plug comprises a wall 610 which is perpendicular to the axis of the conduit and closes off said conduit and on which a rupture initiator 611 is formed. The rupture initiator 611 constitutes an area of weakness along which, under a certain gas pressure, the sealing disk 61 yields and opens out like petals. The rupture or opening threshold for the burstable sealing disk is determined by the depth of the rupture initiator 611 formed on the wall 610. The pyrotechnic charge 62 is placed in the conduit formed by the cartridge 6 between the primer 60 and the burstable sealing disk 61. FIG. 7 shows the body 2 of a device which has functioned and in which the cartridge 6 is empty.

According to the invention, the body 2 comprises, between the percussion device 3 and the expansion chamber 4, a seat which is accessible from the outside of the body 2 and which is intended to receive the gas-generating cartridge 6. This seat follows the right angle defined between the gas expansion chamber 4 and the first vertical branch of the U formed by the body 2. An opening 20 communicating with the seat is formed on the body 2. This opening 20 is formed laterally on the body 2, substantially in the axis of the gas expansion chamber 4. The gas-generating cartridge 6 is intended to be inserted into said opening 20 until it is set into the seat provided for it. The gas-generating cartridge 6 is inserted in such a way that its L-shape follows the right angle formed between the first vertical branch of the inverted U, formed by the body 2, and the gas expansion chamber 4. The cartridge 6, once fitted into the seat, is crimped onto the body 2 at the level of the opening 20. Once in place in the seat, the burstable sealing disk 61 closing off the conduit formed by the cartridge 6 at its downstream end is situated in the axis of the gas expansion chamber 4, and the primer 60 closing off said conduit at its upstream end is situated in the axis of the first subassembly and more particularly in the axis of the striker 30.

By making the seat for the pyrotechnic cartridge 6 accessible from the outside of the body 2, this means that it is possible, during the process of assembling the device, to position the cartridge 6 in the body 2 at any stage of this process. According to the invention, the positioning of the cartridge 6 in the body 2 is done independently of the assembling of the other elements of the device, that is to say, for example, it is not necessary for the cartridge 6 to be placed in the device prior to the percussion device 3.

Thus, according to the invention, it will be possible to adapt the pyrotechnic cartridge 6 as a function of the nature and/or quantity of liquid active principle to be injected and as a function of the depth of skin penetration desired for said active principle. Moreover, it may be of advantage to be able to place the cartridge 6 in the device toward the end of the assembly process in order to avoid manipulation of the cartridge 6, which manipulation may result in the pyrotechnic charge 62 being initiated at the wrong time.

The functioning of such a needleless injection device 1 having components such as those defined in this application is described in detail in French patent application FR 2 815 544. The overall functioning of such a device 1 may, however, be summarized as follows:

At rest, the striker 30 rests, for example, against a stop with the aid of the pretensioned spring 31 whose axis is more or less coincident with the axis of the striker 30. A maneuver on the part of the patient releases the striker 30 which, under the effect of the relaxation of the spring, will strike the primer 60 situated on the same axis. Initiation of the primer 60 then leads to ignition of the pyrotechnic charge 62 contained in the cartridge 6. When a certain gas pressure is reached, the sealing disk 61 opens up along its rupture initiator 611 and thus allows the gases to pass into the expansion chamber 4. Thereafter, the gases, by pushing on the upstream piston plug 51 contained in the tube 50, eject the liquid active principle through the injection system. As is depicted in FIG. 7, to ensure that the gases do not come into contact directly with the upstream piston plug 51 and to thus avoid polluting the liquid active principle contained in the tube 50, a flexible membrane 8 can be provided at the outlet of the gas expansion chamber 4. Under the action of the gases, this flexible membrane 8 is able to deploy inside the tube 50 and push the upstream piston plug 51 present in the tube 50 and thus eject the liquid active principle through the injection system. This flexible membrane constitutes a leaktight wall between the generated gases and the active principle. In FIG. 7, the body depicted is that of a device which has already functioned, that is to say in which the membrane 8 has been deployed and the cartridge 6 has been emptied after combustion of all of the pyrotechnic charge 62.

It will be obvious to those skilled in the art that the present invention allows embodiments in numerous other specific forms without departing from the scope of application of the invention as claimed. Consequently, the present embodiments are to be considered by way of illustration and may be modified within the scope defined by the attached claims, nor need the invention be limited to the details given hereinabove.

The invention claimed is:

1. A pre-filled and disposable needleless injection device, comprising:
   a body supporting or delimiting a plurality of elements forming a circuit of elements,
   the circuit comprising:
   an initiation device,
   a pyrotechnic gas-generating charge,
   a reservoir containing an active principle which is to be injected and a system for injecting the active principle,
   the body comprising a housing situated in the circuit of elements,
   the pyrotechnic charge being contained in a pyrotechnic cartridge, and
   the housing accommodating the pyrotechnic cartridge,
   wherein the housing, the circuit of elements being in an assembled state, is accessible from the outside so that the pyrotechnic cartridge can be inserted into the housing directly in the circuit of elements, independently of the other elements.

2. The device as claimed in claim 1, the body further comprising an opening communicating with the housing.

3. The device as claimed in claim 2, wherein the cartridge, once in place in the housing, closes off the opening in a manner that is sealed with respect to the outside.

4. The device as claimed in claim 1, wherein the housing is placed between the initiation device and the reservoir containing the liquid active principle.

5. The device as claimed claim 1, wherein the circuit of elements follows the shape of an inverted U comprising two parallel branches joined together via a perpendicular transverse branch.

6. The device as claimed in claim 5, wherein the cartridge is inserted into the circuit at right angles to an axis of symmetry of the U formed by the circuit.

7. The device as claimed in claim 5, wherein the cartridge is L-shaped and once inserted, the L-shape of the cartridge follows a right angle present between one of the parallel branches of the inverted U formed by the circuit and the transverse branch.

8. The device as claimed in claim 1, wherein the cartridge has the shape of an L-shaped duct in which the pyrotechnic charge is placed, the L-shaped duct being plugged at one end by a primer and at the other end by a frangible diaphragm.

9. The device as claimed in claim 1, the device for initiating the pyrotechnic charge further comprising a percussion device for striking a primer.

10. The device as claimed in claim 9, wherein the housing in the body, able to accommodate the cartridge, is placed between the percussion device and an expansion chamber for the gases, the expansion chamber being situated upstream of the reservoir.

11. The device as claimed in claim 10, the body further comprising a first hollow part and a second hollow part which are arranged along two parallel axes and connected by a duct, this duct delimiting the housing for the cartridge and the expansion chamber for the gases.

12. The device as claimed in claim 11, wherein the cartridge is placed in the housing in the body in such a way that the primer is situated along an axis of the percussion device and that the diaphragm is situated along an axis of the gas expansion chamber.

\* \* \* \* \*